United States Patent [19]

Leupold

[11] Patent Number: 4,976,893

[45] Date of Patent: Dec. 11, 1990

[54] PROCESS FOR PREPARING CARBOXYLIC ACIDS

[75] Inventor: Ernst I. Leupold, Neu-Anspach, Fed. Rep. of Germany

[73] Assignee: Hoechst Aktiengesellschaft, Frankfurt am Main, Fed. Rep. of Germany

[21] Appl. No.: 875,638

[22] Filed: Jun. 18, 1986

[30] Foreign Application Priority Data

Jun. 20, 1985 [DE] Fed. Rep. of Germany ....... 3522032

[51] Int. Cl.$^5$ .................. C07C 51/235; C07C 53/126; C07C 53/136; C07C 59/70
[52] U.S. Cl. .................................... 260/413; 562/421; 562/499; 562/508; 562/537; 562/538
[58] Field of Search ................ 260/413; 562/508, 538, 562/421, 499, 537

[56] References Cited

U.S. PATENT DOCUMENTS

| | | |
|---|---|---|
| 3,342,858 | 9/1967 | Fuhrmann et al. . |
| 3,407,220 | 10/1968 | Williams et al. . |
| 3,799,977 | 3/1974 | Rutledge . |
| 4,214,101 | 7/1980 | Miya ..................................... 562/538 |
| 4,238,625 | 12/1980 | Fiege et al. . |
| 4,256,916 | 3/1981 | Morris ................................ 562/538 |

FOREIGN PATENT DOCUMENTS

| | | |
|---|---|---|
| 2851788A1 | 6/1980 | Fed. Rep. of Germany . |
| 2936123A1 | 4/1981 | Fed. Rep. of Germany . |
| 3135946 | 3/1983 | Fed. Rep. of Germany . |

*Primary Examiner*—Vivian Garner
*Attorney, Agent, or Firm*—Curtis, Morris & Safford

[57] ABSTRACT

The invention relates to a process for preparing carboxylic acids by platinum-catalyzed oxidation of primary alcohols of limited water solubility with oxygen in a mixture of water and a solubilizer. The solubilizer used is an ether of the general formula $R_1O(CH_2CH_2O)_nR_2$, where n is 1–4 and $R_1$ and $R_2$ are alkyl radicals having 1–4 carbon atoms.

4 Claims, No Drawings

PROCESS FOR PREPARING CARBOXYLIC ACIDS

The present invention relates to a process for preparing carboxylic acids by platinum-catalyzed oxidation of primary alcohols of limited water solubility with oxygen in a mixture of water and a solubilizer.

The preparation of carboxylic acids by oxidizing primary alcohols with oxygen in the presence of platinum catalysts has been known for a long time. In general the reaction is carried out in water as solvent (U.S. Pat. Nos. 3,342,858, 3,799,977, German Offenlegungsschrift No. 2,936,123).

When alcohol and carboxylic acid are of limited water solubility, hydrocarbons are used as solvent (U.S. Pat. No. 3,407,220). However, this is associated with a number of disadvantages. For instance, the reaction proceeds at a reasonably high rate only under elevated oxygen partial pressure; furthermore, the use of hydrocarbons in the presence of oxygen necessitates expensive safety precautions in order to minimize the risk of explosion.

It is also possible to work in water, if the resulting carboxylic acid is first immediately converted into the corresponding alkali metal salt (U.S. Pat. No. 4,238,625). However, the requisite use of bases in molar amounts leads in the course of the subsequent liberation of the desired carboxylic acid with an inorganic acid to the formation of molar amounts of salt, the disposal of which is associated with considerable costs.

It has already been proposed to oxidize primary alcohols of limited water solubility in the presence of a solubilizer in water over platinum catalysts, but no concrete information was provided about the nature of such a component (German Offenlegungsschrift No. 2,851,788).

It was thus an object of the present invention to provide a suitable solubilizer for the oxidation of primary alcohols of limited water solubility with oxygen in water over platinum catalysts.

A suitable solubilizer should have a number of properties:
inertness under the reaction conditions
nonvolatility with excess oxygen at the customary reaction temperatures of 35° to 95° C., in order to avoid the risk of explosion in the vapor space
easy separability from the reaction mixture.

These economically necessary properties appear to rule out customary solubilizers, such as tert.-butanol, acetone, dioxane, tetrahydrofuran, as unsuitable for the purpose mentioned.

The present invention therefore provides a process for preparing carboxylic acids by platinum-catalyzed oxidation of primary alcohols of limited water solubility with oxygen in a mixture of water and a solubilizer, which comprises using as the solubilizer ethers of the general formula $R_1O(CH_2CH_2O)_nR_2$, where n is 1-4 and $R_1$ and $R_2$ are alkyl radicals having 1 to 4 carbon atoms.

Using the process according to the invention, it is now possible to oxidize even sparingly water-soluble primary alcohols in a simple and economical manner. In the process according to the invention the abovementioned use of alkali metal hydroxide is unnecessary, so that the workup does not necessitate the costly disposal of inorganic salts. Compared with the use of a hydrocarbon as solvent or the use of a solubilizer which is volatile under the reaction conditions, the process according to the invention is technically considerably simpler and safer to carry out since the vapor space, in addition to oxygen, chiefly contains water, hence practically avoiding explosive gas mixtures.

The glycol ethers used as solubilizers have the general formula $R_1O(CH_2CH_2O)_nR_2$, where n is 1-4 and $R_1$ and $R_2$ are alkyl radicals having 1-4 carbon atoms. Of these, preference is given to the dimethyl, diethyl or methyl ethyl ethers of the formulae $CH_3O(CH_2CH_2O)_nCH_3$, $C_2H_5O(CH_2CH_2O)_nC_2H_5$ or $CH_3O(CH_2CH_2O)_nC_2H_5$, in particular to the dimethyl ethers. Measured by the criteria of inertness, low volatility and easy separability, glycol ethers having boiling points within the range from 100° to about 250° C., such as diethylene glycol dimethyl ether and triethylene glycol dimethyl ether, are particularly suitable.

It is also possible to use glycol ethers of the general formula $R_1O(CH_2CH_2O)_nR_2$ where $n>4$ and/or $R_1$ and $R_2$ are alkyl radicals having more than 4 carbon atoms; however, owing to the relatively high boiling points, distillative recovery is more expensive.

However, it is also possible to use other ethers, such as, for example, propylene glycol ethers or crown ethers, as solubilizers, if availability and price ensure economical utilization of the process.

The amount of ether used in relation to the amount of water can vary within wide limits. Expediently the amount is chosen to be such that the alcohol used is just completely dissolved at the reaction temperature. This means in general a water/solubilizer ratio between 0.1 and 100.

In principle the process according to the invention can be used to oxidize practically any primary alcohol of limited solubility in water to the corresponding carboxylic acid; alcohols, that is, which carry n- and/or iso-alkyl and/or cycloalkyl and/or aryl substituents and in which additional hetero atoms can also be present.

It is possible to use, for example: aliphatic alcohols, such as 1-pentanol, 2-methyl-1-butanol, 3-methyl-1-butanol, 2,2-dimethyl-1-propanol, 1-hexanol, 2-methyl-1-pentanol, 2-ethyl-1-butanol, 1-heptanol, 1-octanol, 2-ethyl-1-hexanol, isooctanol, 1-nonanol, 1-decanol, 1-undecanol, 1-dodecanol, 1-tridecanol, 1-tetradecanol, 1-pentadecanol, 1-hexadecanol, 1-heptadecanol, 1-octadecanol, 1-nonadecanol, 1-eicosanol, 1-docosanol, 1-tetracosanol, 1-hexacosanol, 1-octacosanol; or glycol ethers of the general formula $RO(CH_2CH_2O)_nH$ where $R=$alkyl, cycloalkyl or aryl and $n \geq 1$, such as butylglycol, pentylglycol, hexylglycol, cyclohexylglycol, 2-ethylhexylglycol, phenylglycol, o-sec.-butylphenylglycol, p-nonylphenylglycol, hexyldiglycol, 2-ethylhexyltriglycol, phenylpolyglycol.

Preferably the alcohols are used in the form of a 10 to 50% strength solution in the mixture of water and solubilizer. Lower concentrations are possible in principle, but as a consequence the expense of isolating the reaction product rises. Higher concentrations are likewise possible; however, the rate of reaction gradually decreases with increasing alcohol concentration.

The reaction temperature is in general between 20° and 150° C.; obtaining the latter temperature may require the employment of superatmospheric pressure. The range from 35° to 95° C. is preferred, since then a particularly high selectivity and reactivity is achieved.

The preferred oxidizing agent is pure oxygen; however, it is also possible to use mixtures of oxygen with inert gases such as air.

Suitable platinum catalysts are commercially available supported catalysts, in particular activated carbons with 5 to 10% by weight of platinum.

The employment of pressure is not absolutely necessary, but the rate of reaction does increase markedly with the oxygen partial pressure. Preference is therefore given to a pressure range from 1 to 10 bar (absolute). At a higher pressure, for example 100 bar, the reaction proceeds even faster; but then the advantage of the higher rate of reaction can be eliminated by the need for higher investment.

The process according to the invention can be carried out in any apparatus which is suitable for carrying out reactions in the liquid phase with or without employment of superatmospheric pressure, for example in a stirred tank or in a bubble column with suspended catalyst; however, it is also possible to use fixed bed reactors with granular catalyst as trickle phase reactors.

The reaction mixture can be worked up by known methods. An expedient method is a distillation, in which water and solubilizer and also unreacted starting material are generally the first to pass over and can be returned into the reactor. Depending on the purity requirements, the carboxylic acid can then be passed to its further use either directly or after a distillative purification.

EXAMPLE 1

An externally heated upright glass tube (diameter: 50 mm, length: 800 mm) which had been filled with a mixture of 200 g of n-octan-1-ol, 175 g of diglycol dimethyl ether and 50 g of a commercially available catalyst (5% platinum on active carbon) was supplied at a temperature of 90° C. and through a glass frit from below with a 25 l (S.T.P.)/h stream of oxygen. The reaction time was 20 h. The filtered reaction solution contained 19.7% by weight of caprylic acid. In the distillative workup the removal of water and diglycol dimethyl ether left 171.4 g of caprylic acid, which corresponds to a yield of 77.4%.

COMPARATIVE EXAMPLE

Example 1 was repeated, except that the solubilizer was replaced by the same amount of water, affording a reaction mixture which contained less than 1% by weight of caprylic acid.

EXAMPLE 2

A mixture of 200 g of 2-phenoxyethanol, 500 g of water, 300 g of diglycol dimethyl ether and 50 g of catalyst was reacted at 80° C. with oxygen for 22 h under the conditions described in Example 1. The filtered reaction solution contained 14.4% by weight of 2-phenoxyacetic acid.

EXAMPLE 3

200 g of ortho-sec.-butylphenoxyethanol in 255 g of water and 545 g of diglycol dimethyl ether were oxidized with oxygen at 80° C. in the presence of 50 g of catalyst in the course of 23 h under the conditions specified in Example 1. The filtered reaction solution was found to contain 16.3% by weight of ortho-sec.-butylphenoxyacetic acid.

EXAMPLE 4

A mixture of 200 g of n-octan-1-ol, 250 g of water, 550 g of tetraethylene glycol methyl tert.-butyl ether and 40 g of catalyst was oxidized at 80° C. with oxygen in the course of 25 h as described in Example 1. The filtered reaction solution contained 18.3% by weight of caprylic acid.

EXAMPLE 5

A mixture of 200 g of 2-ethylhexanol, 650 g of diglycol dimethyl ether, 150 g of water and 50 g of catalyst was reacted at 90° C. with oxygen for 14 h analogously to Example 1. The filtered reaction solution contained 18.3% by weight of 2-ethylhexanoic acid.

EXAMPLE 6

200 g of 2-ethylhexylglycol, 550 g of diglycol dimethyl ether, 250 g of water and 50 g of catalyst were reacted at 80° C. with oxygen for 6 h as described in Example 1:

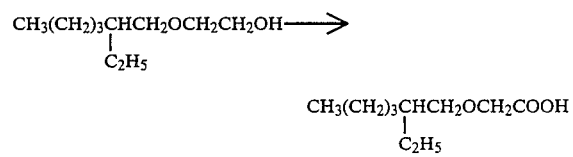

The filtered reaction solution contained 20.6% by weight of 2-ethylhexoxyacetic acid. In the distillative workup the removal of water and diglycol dimethyl ether left 163 g of pure 2-ethylhexoxyacetic acid having a boiling point of 115° C. at 3 mbar which corresponds to a pure yield of 75.4%.

EXAMPLE 7

200 g of a mixture of isomeric p-iso-nonylphenoxyethanols (with differently branched nonyl radical), 600 g of triglycol dimethyl ether, 200 g of water and 50 g of catalyst were reacted at 90° C. with oxygen for 11 h analogously to Example 1

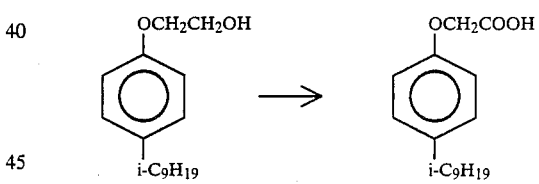

After removal of the catalyst the reaction solution contained 19.2% by weight of isomeric p-iso-nonylphenoxyacetic acids.

EXAMPLE 8-10

An externally heated upright glass tube (diameter: 25 mm, length: 200 mm) which had been filled with a mixture of 35 ml of diglycol dimethyl ether, 5 ml of $H_2O$, 2.5 g of a catalyst (5% of Pt on active carbon) and 10 g of a mixture of isomers of alcohols of the same number of carbons with primary hydroxyl groups, as obtained for example from the hydroformylation of olefin mixtures and subsequent hydrogenation, was supplied at 80° C. and through a glass frit from below with a 10 l (S.T.P.)/h stream of oxygen for a period of 12 h. The filtered reaction solution contained the tabulated amounts of carboxylic acid isomers:

TABLE

| Example | Alcohol | Carboxylic acid | Content [% by weight] |
|---|---|---|---|
| 8 | Isotridecanol | Isotridecanoic | 18.1 |

TABLE-continued

| Example | Alcohol | Carboxylic acid | Content [% by weight] |
| --- | --- | --- | --- |
| 9 | Isohexadecanol | Isohexadecanoic acid | 18.6 |
| 10 | Isooctadecanol | Isooctadecanoic acid | 19.8 |

EXAMPLE 11

10 g of 8-hydroxymethyltricyclo[5.2.1.0$^{2.6}$]decane were treated at 80° C. with oxygen in the presence of 30 g of diglycol dimethyl ether, 10 g of water and 2.5 g of catalyst for 14 h analogously to Examples 8–10. The filtered reaction solution contained 19.1% by weight of 8-carboxytricyclo[5.2.1.0$^{2.6}$]decane.

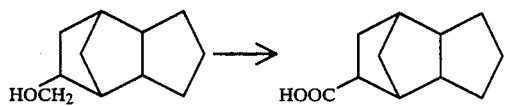

EXAMPLE 12

10 g of a mixture of p-iso-nonylphenylpolyglycols of the general formula i-C$_9$H$_{19}$

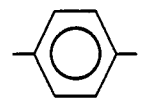

(OCH$_2$CH$_2$)$_n$OH where n=3–8, together with 15 g of diglycol dimethyl ether, 25 g of water and 2.5 g of catalyst, were reacted at 60° C. with oxygen for 10 h analogously to Examples 8–11. The filtered reaction solution contained 18.3% by weight of a mixture of the corresponding p-iso-nonylphenylpolyglycolic acids.

I claim:

1. A process for preparing carboxylic acids by platinum-catalyzed oxidation of primary alcohols of limited water solubility with oxygen in a mixture of water and a solubilizer which comprises using as the solubilizer ethers of the formula R$_1$O(CH$_2$CH$_2$O)$_n$R$_2$, where n is 1–4 and R$_1$ and R$_2$ are alkyl radicals having 1–4 carbon atoms.

2. The process as claimed in claim 1, wherein diethylene glycol dimethyl ether is used as the solubilizer.

3. The process as claimed in claim 1, wherein the water/solubilizer ratio is between 0.1 and 100.

4. The process as claimed in claim 1, wherein triethylene glycol dimethyl ether is used as the solubilizer.

* * * * *